(12) United States Patent
Winter et al.

(10) Patent No.: US 8,933,081 B2
(45) Date of Patent: Jan. 13, 2015

(54) MELTING TABLET CONTAINING A SILDENAFIL SALT

(75) Inventors: Sven Winter, Neubeckum (DE); Max-Werner Scheiwe, Maulburg (DE)

(73) Assignee: ratiopharm GmbH, Ulm (DE)

( * ) Notice: Subject to any disclaimer, the term of this patent is extended or adjusted under 35 U.S.C. 154(b) by 281 days.

(21) Appl. No.: 13/262,971

(22) PCT Filed: Mar. 31, 2010

(86) PCT No.: PCT/EP2010/002081
§ 371 (c)(1),
(2), (4) Date: Dec. 2, 2011

(87) PCT Pub. No.: WO2010/115576
PCT Pub. Date: Oct. 14, 2010

(65) Prior Publication Data
US 2012/0071488 A1    Mar. 22, 2012

(30) Foreign Application Priority Data
Apr. 6, 2009 (DE) .......................... 10 2009 016 584

(51) Int. Cl.
*A61K 31/497* (2006.01)
*A61K 31/519* (2006.01)
*A61K 9/00* (2006.01)
*A61K 9/20* (2006.01)

(52) U.S. Cl.
CPC ............ *A61K 31/519* (2013.01); *A61K 9/0056* (2013.01); *A61K 9/2027* (2013.01); *A61K 9/2054* (2013.01)
USPC ....... 514/252.16; 424/481; 424/482; 424/483

(58) Field of Classification Search
USPC .............................. 514/252.16; 424/481–483
See application file for complete search history.

(56) References Cited

U.S. PATENT DOCUMENTS

2006/0165781 A1 *   7/2006  Ferran ........................... 424/464

FOREIGN PATENT DOCUMENTS

| IN | 1005/MUM/2002 A | 11/2004 | |
|---|---|---|---|
| WO | WO 00/54777 | * 9/2000 | ........... A61K 31/505 |

* cited by examiner

*Primary Examiner* — Johann R Richter
*Assistant Examiner* — Danielle Sullivan
(74) *Attorney, Agent, or Firm* — Milstein Zhang & Wu LLC

(57) ABSTRACT

The invention relates to an orodispersible tablet comprising the components pharmaceutically acceptable sildenafil salt (a), polymeric adsorbent (b), in particular cation exchanger resin, sweetener (c), and flavoring (d) and, preferably, mucilage (e) and glidant (f). The invention furthermore relates to a process for the preparation of orodispersible tablets comprising a pharmaceutically acceptable sildenafil salt and to the use of a combination of cation exchanger resin and mucilage for masking the flavor of medicaments for treating erectile dysfunction.

12 Claims, No Drawings

MELTING TABLET CONTAINING A SILDENAFIL SALT

The invention relates to an orodispersible tablet comprising the components pharmaceutically acceptable sildenafil salt (a), one or more polymeric adsorbents (b), in particular cation exchanger resin, one or more sweeteners (c), and one or more flavorings (d) and, preferably, one or more mucilages (e) and one or more glidants (f). The invention furthermore relates to a process for the preparation of orodispersible tablets comprising a pharmaceutically acceptable sildenafil salt and to the use of a combination of cation exchanger resin and mucilage for masking the flavor of medicaments for treating erectile dysfunction.

The IUPAC name of sildenafil [INN] is 1-{[3-(1-methyl-7-oxo-3-propyl-6,7-dihydro-1H-pyrazolo[4,3-d]pyrimidin-5-yl)-4-ethoxyphenyl]sulfonyl}-4-methylpiperazine. The chemical structure for sildenafil is shown in formula (1) hereinbelow:

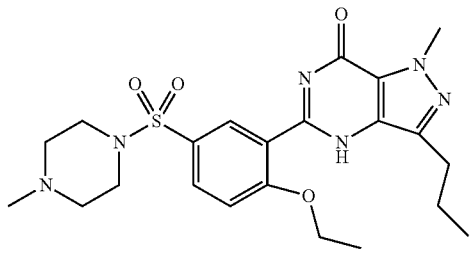

(1) sildenafil

Sildenafil is a potent selective inhibitor of cGMP-specific phosphodiesterase type 5 (PDE-5), which is responsible for lowering the cGMP level in the corpus cavernosum. Sildenafil is sold under the trade name Viagra® for the treatment of erectile dysfunction.

The prior art proposes various formulations for PDE-5 inhibitors, in particular for sildenafil. WO 2007/02125 describes sublingual tablets which comprise PDE-5 inhibitors such as, for example, sildenafil citrate. However, the prepared tablets mentioned in the examples have a bitter taste which is unacceptable for the patient.

To mask the bitter flavor, WO 98/030209 proposes an oral pharmaceutical form which comprises an active-substance-comprising core, an inner coating layer and an outer coating layer, the outer coating layer comprising a saliva-insoluble polymer.

However, the preparation of the proposed oral pharmaceutical form is technically very complex, which is undesirable.

WO 03/072084 A1 and WO 2004/017976 A1 describe a process for the preparation of rapidly disintegrating tablets, where, initially, sildenafil granules are prepared by means of wet granulation, and these granules are then mixed with pregranulated disintegrant. The disclosed process is technically complex and, moreover, only makes possible a limited active substance content. The masking of the flavor of the active substance is achieved by adding a counterion for reducing the solubility and by adding a pH-increasing additive (sodium carbonate).

However, all of the possibilities proposed in the prior art of masking the flavor of soluble sildenafil salts are unsatisfactory; see EP 0 960 621 A1. Accordingly, EP 0 960 621 A1 and EP 1 120 120 A1 propose the use of the active substance sildenafil as the free base. Because the free base is insoluble, sildenafil is flavorless, and the necessity of the insufficient masking of the bitter taste is thereby overcome. However, the use of water-insoluble active substances is frequently undesired, for example in respect of a rapid onset of action.

In summary, it can be said that the formulations proposed in the prior art have disadvantages. It is therefore an object of the invention to overcome these disadvantages.

Specifically, it is an object of the present invention to provide an oral pharmaceutical form with a short disintegration time. It is intended to prepare the oral pharmaceutical form such that it has a high active substance content. It is intended to avoid using the free sildenafil base.

It is furthermore an object of the invention to provide an oral pharmaceutical form which provides an acceptable flavor for the patient (i.e. the patient should not perceive any bitter flavor).

It is intended to make possible the acceptable flavor even when using a sugar-free formulation.

Finally, it is intended to achieve the abovementioned objects by means of a technically simple (and therefore economic) process in high space-time yields.

It is possible to achieve the objects by the preparation of an orodispersible tablet comprising a pharmaceutically acceptable salt of sildenafil and further pharmaceutical adjuvants, in particular by means of direct compression.

The invention therefore relates to an orodispersible tablet comprising the components
(a) pharmaceutically acceptable sildenafil salt;
(b) polymeric adsorbent;
(c) sweetener; and
(d) flavoring;
and optionally mucilage (e) and/or glidant (f).

The invention furthermore relates to a process for the preparation of an orodispersible tablet comprising a pharmaceutically acceptable salt of sildenafil, comprising the steps:
(i) mixing a pharmaceutically acceptable sildenafil salt with pharmaceutical adjuvants, and
(ii) compressing the mixture,
the processing being carried out in the absence of solvents.

Finally, the invention relates to the use of a combination of cation exchanger resin and mucilage for masking the flavor of medicaments for treating erectile dysfunction, in particular for masking the flavor of sildenafil citrate.

As illustrated hereinabove, the present invention relates to an orodispersible tablet. The expression "orodispersible tablet [Schmelztablette]" is understood as meaning, for the purposes of the present invention, an orodispersible tablet as defined in the European Pharmacopoeia, 6th edition, basic volume 2008. An orodispersible tablet is, therefore, an oral tablet which disintegrates in the oral cavity. The orodispersible tablet is a non-(film)coated tablet.

In accordance with Ph. Eur. 6th edition, orodispersible tablets must be disintegrated in 3 minutes. Within the scope of the present invention, it is preferred that the orodispersible tablets according to the invention have a disintegration time of less than 30 seconds, in particular less than 20 seconds, in the mouth.

The disintegration time is determined as described in Ph. Eur. 6th edition, chapter 2.9.1, test A. If reference is made within the scope of the present application to the average disintegration time, this is understood as meaning the mean of the determination of the disintegration time of 10 tablets.

The orodispersible tablets according to the invention usually have a total weight of less than 1000 mg, more preferably less than 750 mg, in particular less than 500 mg. Usually the orodispersible tablets according to the invention have a weight of more than 50 mg, preferably 100 mg or more, in particular more than 150 mg.

The weight ratio of active substance to auxiliaries in the orodispersible tablets according to the invention is usually from 4:1 to 1:5, preferably from 2:1 to 1:3, in particular from 1:1 to 1:2.

The orodispersible tablets according to the invention must therefore clearly be distinguished from what are known as "chewable tablets" since the latter are usually heavier (approximately 1.5 to 3 g) and usually have a longer disintegration time.

The orodispersible tablets according to the invention usually have a hardness of from 25 to 80 N, preferably of from 35 to 70 N, more preferably of from 40 to 65 N, in particular of from 45 to 60 N. The hardness is usually determined as specified in Ph. Eur. 6th edition, chapter 2.9.8. If reference is made within the scope of the present application to the mean hardness, this is understood as meaning the mean of the determination of the hardness of 10 tablets.

Moreover, the resulting tablets preferably have a friability of less than 5%, especially preferably of less than 3%, in particular of less than 1%. The friability is determined as specified in Ph. Eur. 6.0, section 2.9.7.

The orodispersible tablet according to the invention comprises, as component (a), a pharmaceutically acceptable sildenafil salt.

Examples of pharmaceutically acceptable salts are ammonium salts, hydrochlorides, carbonates, hydrogencarbonates, acetates, lactates, butyrates, propionates, sulfates, methanesulfonates, citrates, tartrates, nitrates, sulfonates, oxalates and/or succinates.

It is especially preferred to use sildenafil citrate and sildenafil hydrochloride. Sildenafil citrate is used in particular. In addition, solvates or hydrates of the abovementioned salts may be used as component (a).

The orodispersible tablets according to the invention comprise component (a) usually in an amount of from 20 to 70% by weight, preferably of from 25 to 60% by weight, in particular of from 28 to 55% by weight, based on the total weight of the orodispersible tablet. The orodispersible tablets according to the invention furthermore usually comprise component (a) in an amount of from 25 to 250 mg, more preferably of from 50 to 150 mg. In particular the orodispersible tablets according to the invention comprise 25 mg, 50 mg or 100 mg of component (a), based on the sildenafil-base content. For example, 35.12 mg of sildenafil citrate corresponds to a converted value of 25 mg of sildenafil-base.

The orodispersible tablets according to the invention comprise, as component (b), a polymeric adsorbent. In general, this is understood as meaning a polymeric substance (i.e. a substance with more than two repeating monomer units) which is capable of adsorbing onto component (a).

The polymeric adsorbent is preferably a hydrophilic polymer.

These are understood as being polymers which include hydrophilic groups. Examples of suitable hydrophilic groups are hydroxyl, amino, carboxylic acid or carboxylate (hereinbelow also referred to as carboxyl/carboxylate), sulfonic acid or sulfonate (hereinbelow also referred to as sulfonic acid/sulfonate). The polymer (b) furthermore preferably has a number-average molecular weight of from $10^3$ to $10^{20}$ g/mol, more preferably of from $10^6$ to $10^{18}$ g/mol. The polymer (b) may be linear or, preferably, crosslinked. In the latter case, the polymer (b) preferably has a degree of crosslinking of from 0.01 to 10%, in particular of from 0.1 to 5%. (Degree of crosslinking=number of carbon atoms which are attached to more than one chain/total number of carbon atoms in the polymer chain).

In a preferred embodiment, the polymeric adsorbent (b) is an ion-exchanger resin. An ion-exchanger resin is a polymer by means of which dissolved ions can be replaced by other ions with the same type of charge.

More preferably, a cation exchanger resin is used as component (b). A cation exchanger resin is understood as being a polymer which comprises functional groups with a cation capable of dissociating away from the former. Examples of these functional groups are sulfonic acid groups/sulfonate groups or carboxyl groups/carboxylate groups. Thus, it is preferred to use, as component (b), a polymer which comprises carboxyl groups/carboxylate groups and/or sulfonyl groups/sulfonate groups. If carboxylate or sulfonate groups are present, then, for example, ammonium, alkali metal and alkaline earth metal ions may act as counterions, with sodium and potassium, in particular potassium, being preferred. Sodium starch glycolate is not a polymeric adsorbent (b) for the purposes of the present invention.

In an especially preferred embodiment, the polymeric adsorbent (b) is a copolymer obtainable by copolymerization of methacrylic acid and divinylbenzene. Such a copolymer is known by the name Polacrilin. Polacrilin in the form of the potassium salt (Polacrilin potassium, in particular as described in the monograph of the US Pharmacopeia) is used in particular within the scope of the present invention.

Polacrilin potassium can be illustrated by the following structural formula

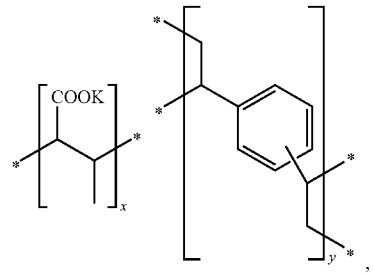

where x and y are natural numbers, for example from $10^1$ to $10^{20}$, preferably from $10^6$ to $10^{18}$. The ratio of x to y is usually 50:1 to 1:1, preferably 20:1 to 2:1, especially preferably 10:1 to 3:1.

Usually, the polymeric adsorbent (b) is used in the orodispersible tablets according to the invention in an amount (b) of from 1 to 60% by weight, preferably of from 5 to 50% by weight, more preferably of from 8 to 45% by weight, especially preferably of from 10 to 40% by weight, and in particular of from 15 to 35% by weight, based on the total amount of the orodispersible tablet.

The orodispersible tablets according to the invention comprise, as component (c), one or more sweetener(s). In general sweeteners refer to substances which normally bring about a sweet taste sensation in the patient when taken.

It is preferred to use sweeteners which have a sweetening power of from 0.2 to 13 000, preferably of from >1 to 4000, in particular of from 10 to 3000, based on the sweetening power of sucrose (=1.0).

Examples are lactose (0.27-0.3), glycerol (0.5-0.8), D-glucose (0.5-0.6), maltose (0.6), galactose (0.6), invert sugar (0.8-0.9), sucrose (1.0), xylitol (1.0), D-fructose (1.0-1.5), sodium cyclamate (30), D-tryptophan (35), chloroform (40), glycyrrhizin (50), acesulfame (130), aspartame (180-200), dulcin (200), Suosan® (350), saccharin (sodium salt) (400-500), saccharin (ammonium salt) (600), 1-bromo-5-nitroaniline (700), naringin dedehydrochalcon (1000-1500), thaumatin, monellin (peptide) (3000), P-4000, n-propoxy-2-amino-4-nitrobenzene (4000), alitame (3000) and/or neotame (13 000). The numerical value in parentheses indicates the sweetening power based on sucrose. It is also possible to use thaumatin and/or neohesperidin DC.

In the orodispersible tablet according to the invention, component (c) is usually employed in an amount of from 0.01 to 10% by weight, more preferably of from 0.1 to 5% by weight, in particular of from 0.5 to 2% by weight, based on the total weight of the tablet.

In a preferred embodiment, the orodispersible tablet according to the invention comprises a plurality of different sweeteners, the tablet according to the invention especially preferably comprising 2, 3 or 4 different sweeteners.

In a more preferred embodiment, components (c) comprises
(c-1) a sweetener with instant sweetness and
(c-2) a sweetener with delayed sweetness.

Components (c-1) and (c-2) may usually be employed in a weight ratio of from 5:1 to 1:5, preferably of from 3:1 to 1:3.

Examples of a sweetener with immediate sweetness (c-1) are saccharine-sodium salt, saccharine-ammonium salt, sucralose, neotame, alitame, aspartame, cyclamate, thaumatin and/or acesulfame.

Examples of sweeteners with delayed sweetness (c-2) are glycyrrhizin or derivatives thereof, in particular glycyrrhizin in the form of the mono-ammonium salt, thaumatin and neohesperidin DC.

The orodispersible tablets according to the invention comprise, as component (d), one or more flavoring(s). Within the scope of the application, the expression "flavoring(s)" is to be understood as defined in the Council Directive 88/388/EEC "flavorings" of Jun. 22, 1988.

Flavoring (d) can be obtained as follows:
i) by means of suitable physical methods (including distillation and extraction with solvents) or by enzymatic or microbiological methods from substances of vegetable or animal origin which are used as such or which are processed for human consumption by means of traditional food preparation processes (including drying, roasting and fermentation);
ii) by means of chemical synthesis or by isolation using chemical processes, where their chemical composition is identical to a substance which naturally occurs in a substance of vegetable or animal origin within the meaning of item i);
iii) by means of chemical synthesis, but where their chemical composition is not identical to a substance which naturally occurs in a substance of vegetable or animal origin within the meaning of i).

In this context, a flavoring may be composed of one or, preferably, more than one chemical compound. For example, peppermint flavoring may comprise a collection of more than 10 chemical compounds.

In the orodispersible tablet according to the invention, component (d) is usually employed in an amount of from 0.001 to 5% by weight, more preferably of from 0.1 to 4% by weight, in particular of from 0.2 to 2% by weight, based on the total weight of the tablet.

In a preferred embodiment, the orodispersible tablet according to the invention comprises a plurality of different flavorings (i.e. a plurality of different flavors), the tablet according to the invention especially preferably comprises 2, 3 or 4 different flavorings.

Preferred combinations of flavorings are, for example, peppermint flavoring together with menthol flavoring, peppermint flavoring together with lemon flavoring, peppermint flavoring together with menthol flavoring and lemon flavoring, spearmint flavoring together with lemon flavoring, spearmint flavoring together with menthol flavoring, spearmint flavoring together with lemon flavoring and menthol flavoring, grapefruit flavoring together with peppermint flavoring, grapefruit flavoring together with menthol flavoring and peppermint flavoring, grapefruit flavoring together with spearmint flavoring, grapefruit flavoring together with spearmint flavoring and menthol flavoring.

In a preferred embodiment, the orodispersible tablet according to the invention furthermore comprises one or more than one mucilage(s) (as component (e)). Within the scope of the present invention, mucilages are understood as meaning substances which, by increasing the viscosity or by enveloping, reduce the contact of medicinal substances with the lingual papillae. This usually results in a reduced intensity of the taste sensation.

In one embodiment which is possible, substances which as 2% by weight strength solution or mixture in distilled water lead to a viscosity of more than 2 mPa/s, preferably more than 4 mPa/s, in particular more than 6 mPa/s, measured at 25° C. as specified in Ph. Eur. 6th edition, chapter 2.2.10, are selected as component (e).

The mucilages (e) which can preferably be used are natural gums, cellulose derivatives, alginates and/or nonionic hydrocolloids.

Examples of mucilages (e) are agar, alginic acid, alginate, chicle, carrageenan, dammar, marshmallow extract, gellan (E 418), guar gum (E 412), gum Arabic (E 414), Psyllium seed gum, spruce fat gum, locust bean gum (E 410), karaya (E 416), conjac meal (E 425), obtained from conjac roots, tara gum (E 417), tragacanth (E 413), xanthan gum (E 415), preferably prepared by bacterial fermentation, guar gum and/or lecithin.

Mucilages based on cellulose derivatives which are used are, for example, carboxymethylcellulose, hydroxyethylcellulose and/or methylcellulose.

Gum Arabic is especially preferably used as component (e).

In the orodispersible tablet according to the invention, component (e) is usually used in an amount of from 0 to 15% by weight, more preferably of from 0.1 to 10% by weight, in particular of from 0.5 to 5% by weight, based on the total weight of the tablet.

In one embodiment which is possible, the orodispersible tablet according to the invention comprises more than one different mucilages, the tablet according to the invention especially preferably comprises 2 or 3 different mucilages.

In a preferred embodiment, the orodispersible tablet according to the invention furthermore comprises a glidant (as component (f)). In this context, glidants act as agents which improve the flowability of the powder (=flow regulator) and/or as lubricant.

The purpose of flow regulators (f) is to reduce, in a tableting mixture, not only the interparticulate friction (cohesion) between the individual particles, but also the adhesion of the latter to the wall areas of the mold. An example of an addition for improving the flowability of the powder is disperse silica. It is preferred to use silica with a specific surface area of from 50 to 400 $m^2/g$ as determined by gas adsorption of Ph. Eur., 6th edition, 2.9.26. In this context, it has unexpectedly been found that the use of silica with a specific surface area of from 50 to 400 $m^2/g$ advantageously allows the amount of filler to be reduced.

Furthermore, it is possible to employ, as component (f), lubricants. Lubricants generally serve to reduce the sliding friction. In particular, it is intended to reduce the sliding friction which exists, during tableting, firstly between the stamps which reciprocate within the die chamber and the die wall and, secondly, between the tablet band and the die wall. Examples of suitable lubricants are, for example, stearic acid, adipic acid sodium stearyl fumarate, magnesium stearate and/or calcium stearate.

In the orodispersible tablet according to the invention, component (f) is usually employed in an amount of from 0 to 10% by weight, more preferably of from 0.1 to 5% by weight, in particular of from 1.0 to 3% by weight, based on the total weight of the tablet.

The orodispersible tablet according to the invention may be composed of components (a) to (d) and optionally (e) and (f). However, the tablet according to the invention may optionally comprise further customary pharmaceutical adjuvants.

Examples of these are disintegrants, fillers and acidifiers.

In general, the expression disintegrant refers to substances which accelerate the disintegration of a dosage form, in particular of a tablet, after it has been introduced into water. Examples of suitable disintegrants are organic disintegrants such as microcrystalline cellulose, starch, pregelatinized starch, sodium carboxymethyl starch, sodium carboxymethylcellulose and crospovidone. It is preferred to use microcrystalline cellulose as the disintegrant. In one embodiment which is possible, it is preferred to dispense with so-called "superdisintegrants", in particular croscarmellose and crospovidone.

The orodispersible tablets according to the invention usually comprise disintegrants, in particular superdisintegrants (for example croscarmellose and crospovidone) in an amount of from 0 to 25% by weight, more preferably of from 1 to 15% by weight, in particular of from 2 to 10% by weight, based on the total weight of the tablet. Alternatively, if microcrystalline cellulose is employed as the disintegrant, the orodispersible tablets according to the invention comprise this substance in an amount of from 0 to 90% by weight, more preferably of from 10 to 75% by weight, in particular of from 20 to 60% by weight.

Fillers are generally understood as meaning substances which serve to form the tablet body in tablets which comprise small amounts of active substance (for example less than 70% by weight). This means that, by "extending" the active substances, fillers generate a sufficient amount of tableting composition. Fillers usually thus serve to obtain a suitable tablet size.

Examples of preferred fillers are lactose, starch, starch derivatives, calcium phosphate, sucrose, calcium carbonate, calcium silicate, magnesium carbonate, magnesium oxide, maltodextrin, calcium sulfate, dextrates, dextrin, dextrose, hydrogenated vegetable oil, kaolin and/or preferably sugar alcohols. Examples of suitable sugar alcohols are mannitol, sorbitol, xylitol, isomalt, glucose, fructose, maltose and mixtures of these. It is especially preferred to use microcrystalline cellulose (unless already used as disintegrant) and calcium silicate as the filler.

The orodispersible tablets according to the invention usually comprise fillers in an amount of from 0 to 30% by weight, more preferably of from 1 to 20% by weight, in particular of from 2 to 10% by weight, based on the total weight of the tablet.

Acidifiers serve to provide an acidic flavor component. Examples of acidifiers are citric acid, tartaric acid and salts of these.

The orodispersible tablets according to the invention usually comprise acidifiers in an amount of from 0 to 15% by weight, more preferably of from 1 to 10% by weight, in particular of from 2 to 5% by weight, based on the total weight of the tablet.

It is the nature of pharmaceutical adjuvants sometimes to have multiple functions in a pharmaceutical formulation. For unambiguous delimitation in the context of the present invention, therefore, the fiction preferably applies that a substance used as a particular adjuvant is not also employed as further pharmaceutical adjuvant at the same time. Thus, for example, mannitol—if employed as filler—will not also be used as sweetener. Likewise, polacrilin—if employed as polymeric adsorbent (b)—will not also additionally be employed as disintegrant (although polacrilin also demonstrates a certain disintegrating action).

In a preferred embodiment, the adjuvants in the orodispersible tablet according to the invention are selected such that the orodispersible tablet according to the invention is free from saccharides.

The invention relates not only to the orodispersible tablet according to the invention, but also to a process for its preparation. The tablet according to the invention is especially preferably prepared by direct compression.

The invention therefore relates to a process for the preparation of an orodispersible tablet comprising a pharmaceutically acceptable salt of sildenafil, comprising the steps
(i) mixing a pharmaceutically acceptable sildenafil salt with pharmaceutical adjuvants, and
(ii) compressing the mixture,
the process being carried out in the absence of solvents.

It is preferred, in step (i) of the process according to the invention, to mix the components
(a) pharmaceutically acceptable sildenafil salt;
(b) polymeric adsorbent, preferably cation exchanger resin;
(c) sweetener;
(d) flavoring;
(e) optionally mucilage; and
(f) optionally glidant.

In principle, everything that has been said above on preferred embodiments of the tablet according to the invention applies to the process according to the invention, for example as regards the nature and the amount of components (a) to (f) and the possible addition of further adjuvants such as disintegrants, fillers and acidifiers.

Step (i) of the process according to the invention involves the mixing of sildenafil salt (a) and pharmaceutical adjuvants. Mixing can be effected in customary mixers. For example, mixing can be effected in mechanical mixers or gravity mixers, for example by means of Turbula® T 10B (Bachofen AG, Switzerland).

In a preferred embodiment of the process according to the invention, components (a) and (b) are mixed with each other before carrying out step (i). This premixing step is carried out, for example, in mechanical mixers or in gravity mixers. When the mixing is carried out in mechanical mixers, times of from 3 to 15 minutes are usually required for obtaining a homogeneous mixture. When using gravity mixers, for example by means of Turbula® T 10B (Bachofen AG, Switzerland) or container mixtures, for example by means of CM 500 (J. Engelsmann AG, Germany) or drum mixers, for examples the drum-hoop mixer type (J. Engelsmann AG, Germany), times of from 10 to 20 minutes are usually required for generating the homogeneous mixture.

The mixing conditions of the "premixing" step (of components (a) and (b)) are usually selected such that at least 50% of the number of the sildenafil salt particles employed are bound to the polymeric adsorbent (preferably cohesively), more preferably at least 80% of the particles, especially preferably at least 95% of the particles, in particular at least 99% of the particles.

Step (ii) involves compressing the mixture (from step (i)), i.e. a compression to give tablets. Compressing can be effected using tableting machines known in the prior art. Compressing is effected in the absence of solvents.

Examples of suitable tableting machines are excenter presses or rotary presses. For example, a Fette machine type 102i (Fette GmbH, Germany) may be used. In the case of rotary presses, a pressing force of from 3 to 50 kN, preferably of from 7.5 to 45 kN, will usually be applied.

If appropriate, the mixture of step (i) may be compacted and granulated before being compressed. Granulation is preferably effected as dry granulation. Alternatively, moist granulation may also be effected.

The process according to the invention ensures a technically advantageous preparation method. Compared with the wet granulation proposed in the prior art, it is technically less complex, and the space-time yield can be improved. The present invention relates not only to the process according to the invention, but also to orodispersible tablets obtainable by the process according to the invention.

Moreover, the inventors have found that a combination of polymeric adsorbent (b), in particular in the form of a cation exchanger resin (b), with a mucilage (d) is advantageously suitable for masking the flavor of medicaments for the treatment of erectile dysfunction (which usually have a bitter taste).

The invention therefore furthermore relates to the use of a combination of polymeric adsorbent, in particular cation exchanger resin and mucilage for masking the flavor of medicaments for treating erectile dysfunction, in particular for masking the flavor of sildenafil citrate.

The invention shall be illustrated by the examples which follow.

EXAMPLES

Orodispersible tablets according to the invention were prepared by means of the process according to the invention. A comparative example without using the polymeric adsorbent was also carried out. The formulations employed and the physical properties of the orodispersible tablets obtained can be seen from the table which follows.

|  | Example 1 | Example 2 | Example 3 | Comparative example 4 |
|---|---|---|---|---|
| Sildenafil citrate | 70.24 mg | 70.24 mg | 70.24 mg | 70.24 mg |
| Polacrilin potassium | 70.0 mg | 70.0 mg | 70.0 mg | — |
| Glycyrrhizin | 0.2 mg | 0.2 mg | — | 0.2 mg |
| Saccharin sodium | 0.2 mg | 0.2 mg | 0.4 mg | 0.2 mg |
| Gum Arabic | 1.5 mg | — | 1.5 mg | 1.5 mg |
| Peppermint flavoring | 0.2 mg | 0.2 mg | 0.2 mg | 0.2 mg |
| Mannitol | — | — | — | 70 mg |
| MCC | 60 mg | 61.5 mg | 60 mg | 60 mg |
| Disperse silica | 2.0 mg | 2.0 mg | 2.0 mg | 2.0 mg |
| Sodium stearylfumarate | 5.0 mg | 5.0 mg | 5.0 mg | 5.0 mg |
| Mean hardness | >40 N | >40 N | >40 N | >40 N |
| Average disintegration time | <30 sec | <30 sec | <30 sec | <60 sec |
| Flavor | pleasant peppermint flavor, not bitter | acceptable peppermint flavor | acceptable peppermint flavor, slightly bitter finish | bitter flavor, unacceptable |

Sildenafil citrate and polacrilin were premixed for 10 min in a gravity mixer (Turbula®) and completed, and mixing continued for a further 30 min. After the addition of magnesium stearate, mixing was continued for a further 2 min. The finished mixture was compressed on a rotary press using biconvex stamps.

Since taste sensations can differ between individuals, ten subjects were used for testing the taste of the examples carried out hereinabove, and the average taste sensation was determined. Tasting was carried out 1 hour after the last meal. All subjects were nonsmokers. The test room had a neutral odor, the temperature was 20° C. The responses were assessed, and the subjects were trained, as described in DIN 10950.

The invention claimed is:

1. An orodispersible tablet with a disintegration time of less than 30 seconds comprising:
   (a) a pharmaceutically acceptable sildenafil salt;
   (b) a polacrilin potassium;
   (c) a sweetener;
   (d) a flavoring component; and
   (e) a natural gum,
   wherein the pharmaceutically acceptable sildenafil salt is present in an amount from 28 to 70% by weight, based on the total weight of the orodispersible tablet, and
   with the proviso that mannitol is absent in the orodispersible tablet.

2. The orodispersible table of claim 1, wherein the polymeric adsorbent is present in an amount of from 10 to 50% by weight, based on the total weight of the orodispersible tablet.

3. The orodispersible tablet of claim 1, wherein the natural gum is present in an amount of from 0.1 to 10% by weight, based on the total weight of the orodispersible tablet.

4. The orodispersible tablet of claim 1 further comprising:
   (f) glidant,
   wherein the glidant is silicon dioxide with a specific surface of from 50 to 400 m$^2$/g.

5. The orodispersible tablet of claim 1, wherein the pharmaceutically acceptable sildenafil salt is sildenafil citrate.

6. A process for the preparation of an orodispersible tablet comprising 28 to 70% by weight, based on the total weight of the orodispersible tablet, of a pharmaceutically acceptable salt of sildenafil, the process comprising the steps of:
   (i) mixing a) a pharmaceutically acceptable sildenafil salt; b) polacrilin potassium; c) a sweetener; d) a flavoring component: e) a natural gum; and f) optionally, a glidant salt with pharmaceutical adjuvants, and
   (ii) compressing the mixture, the process being carried out in the absence of solvents,
   with the proviso that mannitol is absent in the orodispersible tablet.

7. An orodispersible tablet obtained by the process of claim 6.

8. The orodispersible tablet of claim 1, wherein the orodispersible tablet has a hardness of from 30 to 70 Newton.

9. The orodispersible tablet of claim 1, comprising a combination of polacrilin potassium resin and a natural gum in amounts capable of masking the flavor of medicaments for treating erectile dysfunction, wherein the combination masks the flavor of sildenafil citrate.

10. The orodispersible tablet of claim 7, wherein the orodispersible tablet has a disintegration time of less than 30 seconds and a hardness of from 30 to 70 Newton.

11. The orodispersible tablet of claim 1, wherein the tablet further comprising a superdisintegrant in an amount of 1 to 15% by weight and an acidifier in an amount of 1 to 10% by weight.

12. The orodispersible tablet of claim 11, having a friability of less than 5%.

* * * * *